United States Patent [19]
Schudy

[11] Patent Number: 5,238,403
[45] Date of Patent: Aug. 24, 1993

[54] ORTHODONTIC BRACKET

[76] Inventor: George F. Schudy, 909 Dairy Ashford, Ste. 201, Houston, Tex. 77079

[21] Appl. No.: 797,203

[22] Filed: Nov. 25, 1991

[51] Int. Cl.$^5$ ............................................. A61C 3/00
[52] U.S. Cl. ....................................................... 433/8
[58] Field of Search ................ 433/8, 9, 16, 10, 11, 433/12, 13, 14

[56] References Cited

U.S. PATENT DOCUMENTS

| | | | |
|---|---|---|---|
| 4,531,911 | 7/1985 | Creekmore | 433/8 |
| 4,793,804 | 12/1988 | Schudy | 433/8 |
| 4,799,882 | 1/1989 | Kesling | 433/8 |

FOREIGN PATENT DOCUMENTS 9107925 6/1991 PCT Int'l Appl. .................... 433/10

Primary Examiner—Cary E. O'Connor
Attorney, Agent, or Firm—Bill B. Berryhill

[57] ABSTRACT

An improved orthodontic appliance of the twin bracket edgewise type in which a pair of spaced apart brackets are affixed to a pad member adapted for attachment to the surface of a tooth, each of the brackets including a base portion resting against the pad member, upper and lower wing portions projecting outwardly from the base portion and an outwardly opening slot of predetermined height between the upper and lower wing portions for receiving an arch wire in cooperation therewith, the height of the arch wire receiving slot of one of the brackets being greater than the arch wire receiving slot of the other.

6 Claims, 1 Drawing Sheet

ORTHODONTIC BRACKET

BACKGROUND OF THE INVENTION

1. Field of the Invention

The present invention pertains to orthodontic appliances for correcting teeth malalignment. Specifically, the present invention pertains to twin orthodontic brackets of the edgewise type.

2. Brief Description of the Prior Art

For many years the most popular, widely used, effective and mechanically sound orthodontic appliances used in correcting imperfections in the alignment of the teeth have been those appliances generally referred to as the "edgewise" type. Although there are several variations of the edgewise appliance, it normally includes brackets which are attached to each tooth in some fashion and at least one arch wire which spans the teeth engaging a slot in each of the brackets. The arch wire may be affixed to each bracket by connecting wire, resilient band or the like. A typical edgewise bracket is sown in U.S. Pat. No. 3,250,003.

Most edgewise brackets include a base portion affixed to a pad which is adapted for attachment, in any suitable manner, to the outer surface of a tooth. Upper and lower wing portions project outwardly from the base portion defining therebetween an outwardly opening slot or groove for receiving the arch wire. The wing portions provide a means of tying or holding the arch wire in place within the slot. The height of the bracket slot (distance between wing portions) is precisely formed to receive the normal rectangular cross-section arch wire in a very precise or tight fit.

For many years, the height of the slot in edgewise brackets was designed for receiving an arch wire, the edgewise dimension of which was 0.022 inches. Such a wire is relatively stiff and exerts an often unnecessary amount of force on the teeth. Consequently, many orthodontists began using edgewise appliances with slots designed to receive arch wires having an edgewise dimension of 0.018 inches. Through the years, it has become apparent that the larger dimensioned brackets, when used with small wires, had several advantages: greater range and resiliency of the wires used, and less permanent deformation of the arch wires due to occlusive forces during mastication. However, the loose fit between a larger dimension bracket and a small wire results in reduced control of the teeth in certain areas.

U.S. Pat. No. 4,793,804 discloses a bracket having a stepped slot which, in effect, provides a small height slot near the base and a larger height slot at the outer opening thereof. Thus, the stepped slot will accommodate, in the portion of the slot nearest its base, a smaller arch wire in a precision manner, or in the portion of the slot nearest its opening, in a loose fit. For example, an orthodontist may use a small wire with a larger portion of the slot during initial treatment. For intermediate treatment, he may use a small wire with large slots (loose fit) on some teeth and small slots (tight or precision fit) on other teeth. In finishing, a small wire may be used with a small slot on all teeth.

Single brackets of the type shown in the previously mentioned U.S. Pat. Nos. 3,250,003 and 4,793,804 provide maximum effectiveness in the application of tipping and torquing of teeth but are not efficient in rotational control. Thus a number of other types of brackets or appliances have been developed to improve over the inefficient rotation of the typical bracket. One of the most accepted types is the twin bracket which instead of one centrally located bracket, provides a pair of spaced apart brackets on a single tooth. When each of these pairs of brackets is tied to the arch wire, there is a tendency of the tooth to rotate so that the facial surface of the tooth aligns itself with the arch wire.

Twin brackets, which have been used for a considerable period of time, typically incorporate a pair of spaced apart brackets each of which defines a precision arch wire slot. The spaced arch wire slots cooperate to provide the effect of a precision arch wire slot extending the entire length of the bracket base. Each of the brackets is provided with upper and lower tie wings, defining a bracket structure with four tie wings. The tie wings in the effective arch wire slot terminate at the opposed sides of the tooth. With the twin bracket centered in respect to the tooth to be moved, the tie wings are thereby positioned in pairs at opposed sides of the tooth to provide a bracket structure with efficient rotation control.

While twin brackets of the prior art offer substantial advantages in rotational control, they are not without disadvantage. They may require frequent patient visits for adjustment to maintain the necessary force levels for efficient tooth movement. Because of the minimum interbracket width provided the arch wire is not allowed to flex as much as with single brackets. This may cause undue discomfort to the patient. In addition, the typical prior art twin bracket may not permit certain control measures for correcting other tooth misalignment problems. For these and other reasons various modifications have been made in the twin bracket. For example, U.S. Pat. No. 4,531,911 discloses a variation of the twin orthodontic bracket which is claimed to overcome some of these disadvantages.

SUMMARY OF THE INVENTION

In the present invention, an improved orthodontic appliance of the twin bracket edgewise type is disclosed which offers differential control not present in the prior art twin brackets. Like the prior art, a pair of spaced apart brackets are provided to facilitate efficient rotational control. However, unlike twin brackets of the prior art, one of the brackets is provided with an arch wire slot for precision or tight fit and the other bracket is provided with an arch wire slot of substantially greater height for a loose fit. Thus, rotational control is provided while allowing more flexibility in tipping and torquing of the teeth.

The bracket of the present invention thus comprises a pair of spaced apart brackets which are affixed to a pad member adapted for attachment to the surface of a tooth. Each of the brackets includes a base portion resting against the pad member and upper and lower wing portions projecting outwardly from the base portion. An outwardly opening slot of predetermined height is defined between each of the upper and lower wing portions for receiving an arch wire in cooperation therewith. The arch wire receiving slot of one of the brackets is greater in height than the arch wire receiving slot of the other. The smaller of the slots is preferably of a height to receive an arch wire in a precision or tight fit, the greater height slot thus accommodating the arch wire in a relatively loose fit.

The resulting twin bracket provides effective rotational control. In addition, it provides control for tipping and torquing of the teeth but with greater flexibility, by allowing differential control at each of the brackets. This results in greater comfort to the patient, probably less frequent visits to the orthodontist and greater flexibility in the straightening of the patient's teeth. Many other objects and advantages of the invention will be understood from reading the description which follows in conjunction with the accompanying drawings.

DESCRIPTION OF THE PREFERRED EMBODIMENT

Figures 1, 2, 3, 4:
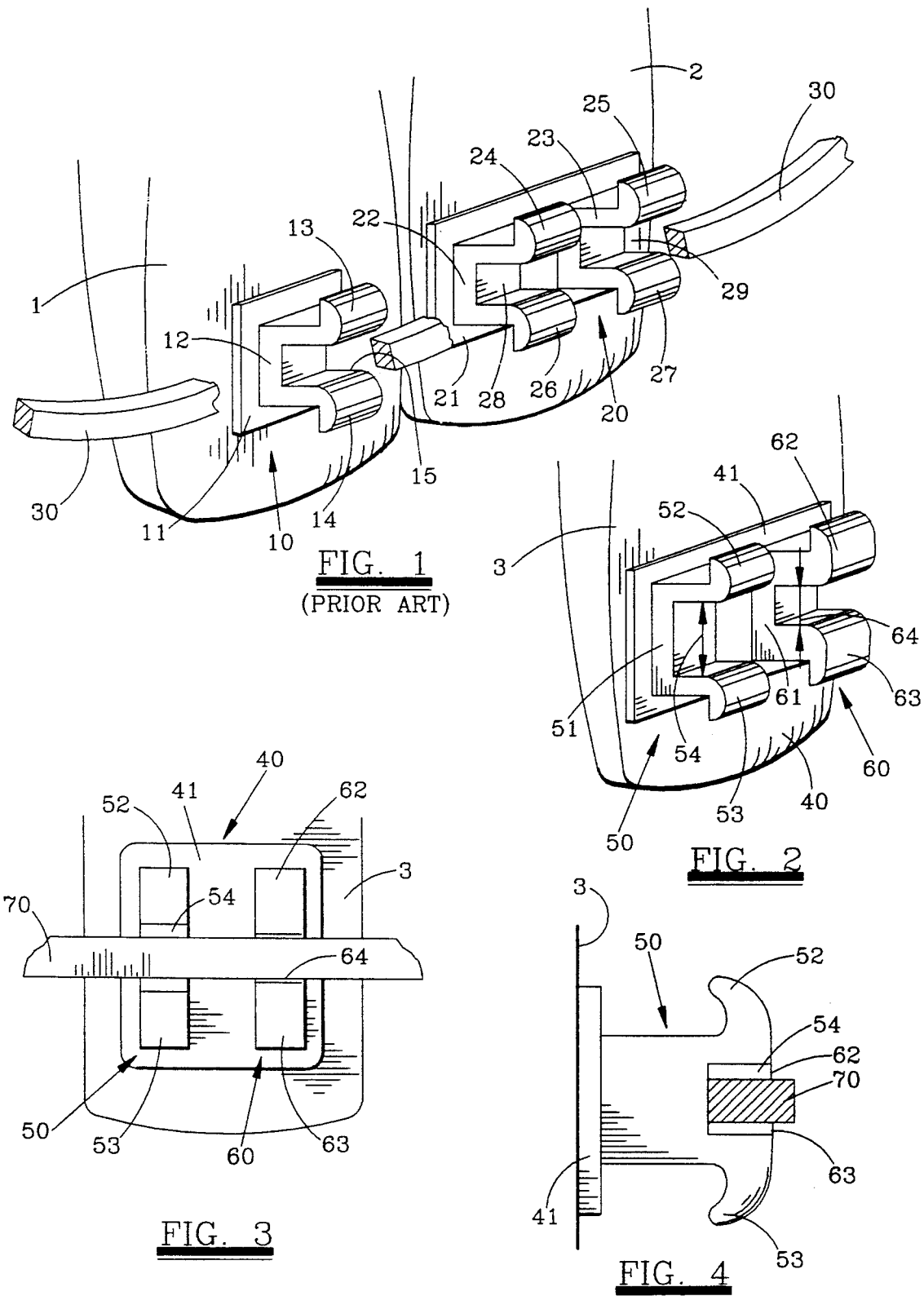
FIG. 1 is a pictorial illustration of a single bracket and twin bracket of the prior art attached to adjacent teeth of a patient.
FIG. 2 is an isometric illustration of an improved orthodontic appliance of the twin bracket edgewise type, according to a preferred embodiment of the present invention.
FIG. 3 is a plan view of the orthodontic bracket of FIG. 2.
FIG. 4 is an end view of the orthodontic bracket of FIGS. 2 and 3.

Referring first to FIG. 1, there is partially illustrated the mouth of a person, whose misaligned teeth 1 and 2 are being corrected by orthodontic appliances of the edgewise type. Attached to tooth 1 is a single bracket appliance 10. Attached to tooth 2 is a twin bracket appliance 20. The single bracket is affixed to a pad 11 which is in turn attached to the tooth in any one of several ways known in the art. The single bracket 10 includes a base portion 12 upper and lower wing portions 13 and 14, between which is defined a rectangular slot 15. The twin bracket 20 is affixed to pad member 21 which is in turn attached to tooth 2. The twin bracket 20 provides a pair of spaced apart brackets each of which includes a base portion 22, 23 upper wing portions 24, 25 and lower wing portions 26, 27, respectively. Defined between the respective wing portions, on each bracket, is a rectangular slot 28, 29. An arch wire 30 (portions of which are broken away for clarity), the ends of which are usually held by a terminal tube provided on the terminal teeth (not shown) is received in the slots 15, 28 and 29 in a precision fit. All of these slots are substantially the same height as the edgewise dimension of the arch wire 30, e.g. 0.018 inches. The single bracket 10 and twin bracket 20 of FIG. 1 are known in the prior art.

Referring now to FIGS. 2, 3 and 4, there is shown a portion of a tooth 3 to which is attached an improved twin bracket 40 of the edgewise type, according to a preferred embodiment of the present invention. This bracket 40 comprises a pair of spaced apart brackets 50, 60 affixed to a pad member 41 which is in turn affixed or attached to the surface of the tooth 3. Each of the brackets 50, 60 includes a base portion 51, 61 resting against the pad member 41. Each of the brackets also has upper wing portions 52, 62 and lower wing portions 53, 63 projecting outwardly from their respective base portions. An outwardly opening slot 54, 64 of predetermined height, is provided between the respective upper and lower wing portions for receiving an arch wire in cooperation therewith, such as the arch wire 30 illustrated in FIG. 1 and the arch wire 70 in FIGS. 3 and 4.

A very important feature of the improved twin bracket of the present invention is the fact that the height of the arch wire receiving slots 54 and 64 are different. As shown in the exemplary embodiment, the slot 54 is substantially greater in height than slot 64. For example, the height of slot 64 may be in the range of 0.014 inches to 0.022 inches and slot 54 may be in a range of 0.022 inches to 0.040 inches. The height of the smaller slot 64 is sized for a precision or tight fit with the arch wire 70 to be used therewith, the slot 54 of substantially greater height then accommodating the arch wire in a relatively loose fit. The plan view of FIG. 3 illustrates this relationship by showing an arch wire 70 placed in the bracket. As can be seen, the arch wire 70 engages the slot 64 of bracket 60 in a precision tight fit and the slot 54 of the other bracket 50 in a very loose fit.

When several twin brackets of the preferred embodiment of the invention, as illustrated in FIGS. 2–4, are used in the same patient's mouth and on adjacent teeth, the brackets would probably be oriented so that the bracket of greatest slot height would always be on the same side of the tooth, at least those on the same side of the mouth. One arrangement might have all twin brackets on one side of the mouth with the slot of greater height to the left while the twin brackets on the other side of the mouth would have the greater height slot to the right. This could afford even greater flexibility of control (and more comfort) between the two central incisors with the greater height slots of the corresponding twin brackets being adjacent each other.

Thus, the twin bracket of the present invention provides an orthodontic appliance of the edgewise type in which none of the efficiency of tooth rotation of twin brackets of the prior art is lost but allows differential control at each of the individual brackets. This allows greater flexibility in control of tipping and torquing of the teeth. It would also reduce friction encountered in sliding the bracket along the arch wire, as is routinely done in orthodontics to redistribute spaces therebetween. All of this would result in more comfort to the patient and probably require fewer visits of the patient to the orthodontist. Both the patient and the orthodontist would benefit from reduced time in the office.

A single embodiment of the invention has been described herein. However, a number of variations of the invention can be made without departing from the spirit thereof. Accordingly, it is intended that the scope of the invention be limited only by the claims which follow.

I claim:

1. An improved orthodontic appliance of the twin bracket edgewise type in which a pair of spaced apart brackets are affixed to a pad member adapted for attachment to the surface of a tooth, each of said brackets including a base portion resting against said pad member, upper and lower wing portions projecting outwardly from said base portion and an outwardly opening slot of predetermined height between said upper and lower wing portions for receiving an arch wire in cooperation therewith, the space between said brackets providing an area for receiving said arch wire without contact therewith; the improvement residing in the height of the arch wire receiving slot of one of said brackets being greater than the arch wire receiving slot of the other.

2. An improved orthodontic appliance as set forth in claim 1 for in which the smaller of said slots is of a height to receive said arch wire in a tight fit, the slot of greater height accommodating said arch wire in a relatively loose fit.

3. An improved orthodontic appliance as set forth in claim 1 for use with an arch wire of rectangular cross-section, the smaller of said slots being of a height substantially the same as the edgewise dimension of said arch wire for receiving said arch wire in a tight fit, the slot of greater height being substantially greater than the edgewise dimension of said arch wire.

4. An improved orthodontic appliance as set forth in claim 1 in which the height of said smaller slot lies in a range of 0.014 inches to 0.022 inches, the height of said larger slot being in a range of 0.022 inches to 0.040 inches.

5. A method of using the improved orthodontic appliance as set forth in claim 1 in which a plurality of said twin bracket appliances are attached to respective teeth in a patient's mouth, the twin bracket appliances on one side of the mouth having greater height slots to the left while the twin bracket appliances on the other side of the mouth have greater height slots to the right.

6. The method of claim 5 in which each one of the two adjacent central incisors have one of said twin bracket appliances attached thereto, the greater height slot of one twin bracket appliance being adjacent to the greater height slot of the other twin bracket appliance.

* * * * *